United States Patent [19]

Emanis et al.

[11] Patent Number: 4,636,203
[45] Date of Patent: Jan. 13, 1987

[54] EARLOBE TREATMENT APPARATUS

[76] Inventors: Russell B. Emanis, 219 Countryside Dr., Arlington, Tex. 76014; Don L. Wallace, 2218 Skybark Dr., Arlington, Tex. 76010; Travis W. Wolfe, 614 Hill City Dr., Duncanville, Tex. 75116; Waverly B. Emanis, 1512 Arbor Town Cir., #517, Arlington, Tex. 76011

[21] Appl. No.: 609,469

[22] Filed: May 11, 1984

Related U.S. Application Data

[63] Continuation-in-part of Ser. No. 567,795, Jan. 3, 1984, abandoned.

[51] Int. Cl.$^4$ ............................................. A61M 5/185
[52] U.S. Cl. ..................................... 604/257; 604/37; 604/263; 604/310
[58] Field of Search ............................. 604/27, 36–37, 604/39, 73, 93, 257, 267, 279, 310, 264, 263; 401/183, 186, 266, 265, 261, 263

[56] References Cited

U.S. PATENT DOCUMENTS

| | | | |
|---|---|---|---|
| 264,904 | 9/1882 | Smith . | |
| 299,046 | 5/1884 | Alderman | 401/261 |
| 619,845 | 2/1899 | Shattuck . | |
| 889,810 | 6/1908 | Robinson | 604/310 |
| 2,291,509 | 7/1942 | Terry | 604/310 |
| 2,450,217 | 9/1948 | Alcorn | 604/93 |
| 2,664,894 | 1/1954 | Garrepy | 604/93 |
| 2,865,373 | 12/1957 | Recker . | |
| 3,187,367 | 6/1965 | Luedtke | 401/186 |
| 3,260,258 | 7/1966 | Berman | 604/93 |
| 3,500,829 | 3/1968 | Abramowitz . | |
| 3,520,629 | 7/1970 | Otsuka | 401/265 |
| 3,698,391 | 10/1972 | Mahony | 604/93 |
| 4,041,946 | 8/1977 | Barton | 604/93 |
| 4,206,756 | 6/1980 | Grossan | 604/39 |
| 4,318,403 | 3/1982 | Sneider | 604/37 |

Primary Examiner—C. Fred Rosenbaum
Assistant Examiner—Gene B. Kartchner
Attorney, Agent, or Firm—Hubbard, Thurman, Turner & Tucker

[57] ABSTRACT

Apparatus for cleaning and treating earlobes which have been pierced to form earring postholes comprising an elongated pinlike probe secured at one end to a plug member which is removably secured in the neck of a flexible walled container for holding and dispensing a cleaning and medicinal treating solution. The probe member is formed with an elongated shank extending from the plug member and having a spherical distal end. In one embodiment the probe is formed of a longitudinal groove defining opposed parallel tissue scraping or reeming surfaces and providing a flow channel for introducing a quantity of solution into the posthole. Another embodiment of the probe is formed with an internal flow channel opening into the longitudinal groove at spaced apart orifices. The plug member can be formed with a generally convex projection and a bore in which the probe is supported to form a flow channel for the treating solution which is sealed by the plug member when pressed against the side of the earlobe to prevent unwanted spillage of treating solution before it is forced through the posthole. The dispensing container may be squeezed to dispense treating solution and is of a cylindrical shape to facilitate ease of rotation of the probe during the insertion and cleaning process.

4 Claims, 6 Drawing Figures

EARLOBE TREATMENT APPARATUS

CROSS-REFERENCE TO RELATED APPLICATION

This application is a continuation-in-part of U.S. Pat. application Ser. No. 567,795, filed: Jan. 3, 1984 now abandoned.

BACKGROUND OF THE INVENTION

1. Field of the Invention

The present invention pertains to an apparatus for use in cleaning and treatment of earlobes which have been pierced to form earring postholes. A slender pinlike probe is formed with a passage for dispensing an antiseptic solution upon insertion into the posthole and is connected to a squeezable syringelike dispenser.

2. Background

The piercing of the human earlobe is widely practiced as means to provide a journal for receiving and supporting an earring or the support post of similar ear ornaments. However, since the formation of the passage or posthole for receiving the earring post creates an unnatural opening in the earlobe there is a tendency over a period of time for the epithelium to close the passage thereby requiring a repiercing operation. The presence of an earring posthole also tends to promote infection of the earlobe from the accumulation of foreign matter in the passage and, in varying degrees, individuals are susceptible to irritation or infection of the earlobe.

In this regard there has been a longfelt need for means for conveniently and easily treating the earlobe to keep the earring posthole clean and free of infection and also keep the passage opening of a size that will permit easy insertion of the earring or ear ornament post. In particular, it has been difficult for persons to properly clean the earring postholes themselves in view of the location of the earlobes but, since it is an exercise which must be practiced frequently by individuals that are susceptible to infection of the earlobe or regrowth of tissue to close the posthole there has been a need for a device which may be easily handled by oneself and not requiring assistance in performing the treatment process. Certain desiderata are evident form prior art practice which have not been previously met with prior art devices. These desiderata incluse the provision of a device which may be easily inserted into the posthole without assistance and without causing pain in the event that the posthole has begun to close. The device should be provided with an antiseptic solution to clean the posthole of foreign matter and to prevent infection or to treat existing infection. Finally, it is desirable that the apparatus perform somewhat of a scraping or reaming function to remove foreign matter. The device should also be capable of reuse and refilling with a treatment solution. These desiderata have been met by the apparatus of the present invention as will be appreciated by those skilled in the art.

SUMMARY OF THE INVENTION

The present invention provides an apparatus for treating earlobes to clean and maintain the earring posthole open to facilitate insertion of an earring or ear ornament post and to reduce the chances of infection or inflamation of the tissue defining the posthole. In accordance with one aspect of the present invention there is provided a slender metal probe which is connected to a flexible dispensing container for supporting the probe and for dispensing a cleaning solution through a passage formed in the probe.

In accordance with another aspect of the present invention there is provided an earring posthole cleaning and treatment apparatus characterized by a slender probe attached to a cleaning solution dispenser and having a passage formed in the probe for conducting the treating solution into the posthole for flushing matter from the posthole and for serving as a germicide to reduce the possibility of infection of the tissue defining the posthole. The probe passage may take various configurations and preferably is formed as a longitudinal groove or grooves opening to the periphery or the external surface of the probe. The groove or grooves may extend to the distal end of the probe and form edges which function to facilitate a scraping or cleaning action of the posthole as the probe is rotated therein. The probe is preferably also formed with a smoothly curved distal end to facilitate insertion of the probe in a clogged or partially blocked posthole to alleviate pain and to provide for ease of penetration of the probe into tissue which is not to be cut. Parallel groove edges formed by the treating solution flow passage are suitably formed to prevent cutting the tissue defining the posthole but to also present scraping edges upon rotation of the probe in the posthole to facilitate cleaning and reaming of the posthole.

In accordance with yet another aspect of the present invention there is provided a device for cleaning postholes for earrings and other ear ornaments wherein a flexible treating solution container is provided which is adapted to support a slender probe for penetrating the posthole and which probe is fixed to a removable plug member for the container which is forcible fitter over the mouth of the container in sealing engagement therewith but which may also be conveniently removed for filling the container with a treating solution. The plug member may be formed with a generally frusto-conical convex surface for engagement with the earlobe tissue around the possible to form a seal whereby a treating solution may be ejected from the bottle through an annular passage formed between the plug member and a portion of the probe extending through the plug member. The container is provided with a removable cap which forms a closure over the probe to protect it from damage or contamination and to allow the probe to be bathed with a quantity of the treating solution to maintain its sterility prior to each use. The dispensing type treating solution container is preferably of a cylindrical form to facilitate manual rotation of the container while holding it in the inserted position of the probe in the posthole to perform the cleaning action of the probe and to thoroughly wet the tissue defining the posthole to cleanse and disinfect same.

Those skilled in the art will recognize the abovedescribed advantages and superior aspects of the invention as well as additional features upon reading the detailed description which follows in conjunction with the drawing.

DESCRIPTION OF THE PREFERRED EMBODIMENTS

Figure 1:
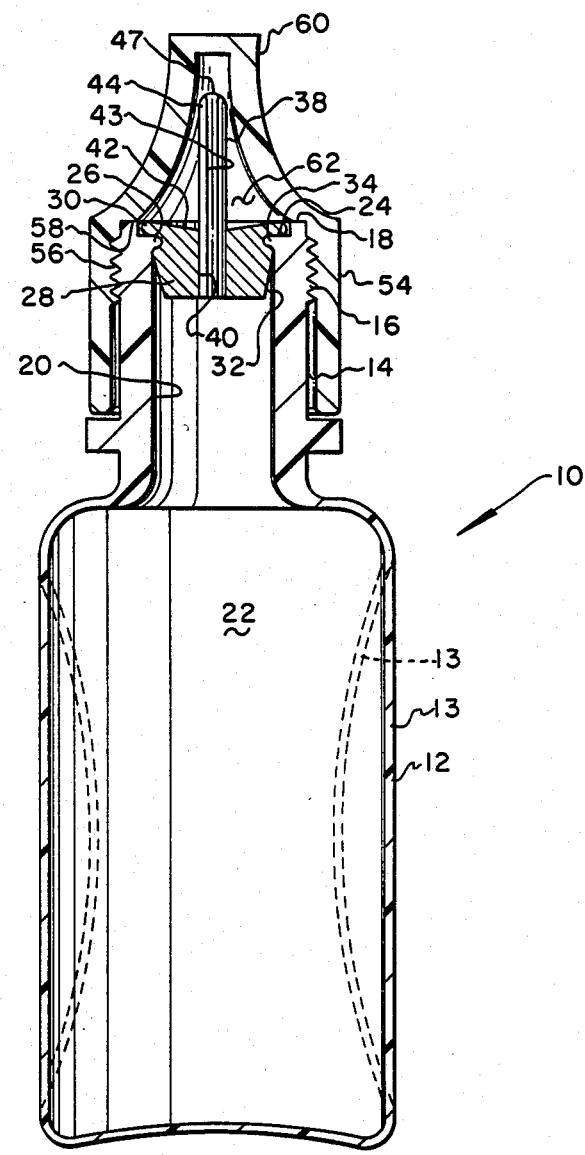
FIG. 1 is a longitudinal central section view of an earlobe treating apparatus in accordance with the present invention.

In the description which follows like parts are marked throughout the specification and drawing with the same reference numerals, respectively. The drawing is not necessarily to scale and certain features of the invention may be exaggerated in scale in the interest of clarity.

Referring to FIG. 1, the apparatus of the present invention is illustrated and generally designated by the numeral 10. The apparatus 10 comprises a flexible syringelike plastic bottle or container 12 of generally cylindrical configuration and having a reduced diameter portion forming a neck 14 which is provided with external threads 16 and a transverse seal shoulder 18. The neck 14 defines a mouth 20 opening into an interior chamber 22 of the container which is adapted to hold a quantity of liquid antiseptic solution. The neck 14 also includes a transverse end face 24 delimited at its outer periphery by the shoulder 18 and at its inner periphery by an annular radially inward projecting rim 26. The end face 24 and the rim 26 are adapted to cooperate with a removable, generally cylindrical metal or plastic plug member 28 having a cylindrical flange 30 and a somewhat frusto-conical shaped hub portion 32 which is undercut at it junction with the flange 30 to form a circumferential groove 34. The plug 28 is forcibly insertable into the mouth 20 wherein the frusto-conical hub portion 32 engages the inner diameter of the rim 26 to elastically deflect the neck 14 radially outwardly until the rim 26 snaps into the groove 34 whereby the plug 28 is forcibly engaged with the neck to form a fluid-tight seal, at least between the flange 30 and the end face 24. The dimensional proportions of the rim 26 with respect to the hub portion 32 and the groove 34 are such that the plug 28 may be inserted in and removed from the mouth 20 in the neck 14 to form a substantially fluid-tight closure for the container 12.

The apparatus 10 is also provided with a unique elongated pinlike probe member 38 which is supported by the plug 28 and projects into a central bore 40 extending through the plug 28. The plug 28 is also preferably formed with a conical recess 42 in the flange 30 and tapering toward the bore 40. The probe 38 is characterized as an elongated metal pin member having a longitudinally extending somewhat V-shaped groove 43 extending the length thereof and opening to the distal end 44 of the probe and to the opposite end of the probe into the interior chamber 22 when the assembly of the probe 38 and the plug 28 are supported by the neck 14.

Figure 3:
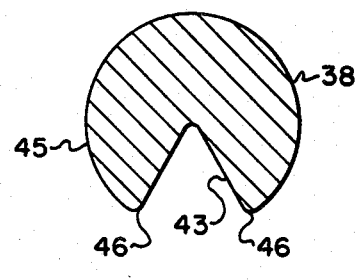
FIG. 3 is a transverse section view of the probe taken along the line 3—3 of FIG. 2.

Referring also to FIGS. 1 and 3, the distal end 44 of the probe 38 illustrated as being formed by a hemispherical surface 47 which is intersected by the groove 43. The groove 43 also opens to the cylindrical outer circumference of the probe 38 along its length. The intersection of the flanks of the groove 43 with the outer circumferential surface 45 of the probe 38 is preferably formed by slight curved edges 46, FIG. 3, to avoid a sharp cutting edge but to provide a sufficient rake angle between the flanks of the groove 43 and the surface 45 to allow the edges 46 to perform a scraping function when the probe is inserted in a posthole in an earlobe and rotated about the probe longitudinal axis. The intersection of the flanks of the groove 43 with the distal end surface 47 of the probe 38 is also provided with slight curved edges 50 to avoid a sharp edge which might make an unwanted incision in the earlobe as a result of a partially restricted posthole.

Figure 2:
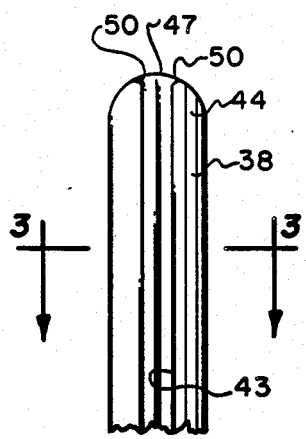
FIG. 2 is a detail elevation view of the distal end of the probe of the apparatus of FIG. 1.

The embodiment of the probe 38 illustrated in FIGS. 1, 2 and 3 is a substantially solid cylindrical pin member which is preferably formed from an inert metal such as stainless steel or a gold or silver alloy to give the probe sufficient strength for its relatively small diameter and to prevent corrosion and the harboring of bacteria on the surface of the probe. The diameter of the probe 38 may vary in a range of from approximately 0.005 inches to as great as 0.125 inches. The groove or channel 43 may be formed by a machining operation or by an extrusion or drawing operation during the formation of the probe 38. The curved edges 46 and 50 may be formed by a suitable finishing or deburring operations after the formation of the groove 43. The full rounded or spherical end surface 47 may also be formed by a suitable metal forming operation prior to the finishing or deburring step.

The probe 38 is preferably demensioned to be an interference fit in the bore 40 of the plug 28 to form an assembly which may be inserted in and removed from the neck 14 for filling the container 12 with a suitable treating solution. As shown in FIG. 1, the apparatus 10 is preferably provided with a protective cap 54 having internal threads 56 cooperating with the threads 16 and a transverse annular shoulder 58 cooperable with the shoulder 18 to form a fluid-tight seal when the cap is threaded on the neck 14. The cap 54 includes an axially projecting spire portion 60 to accommodate the probe 38 within a chamber 62 when the apparatus 10 is not in use.

Figure 6:
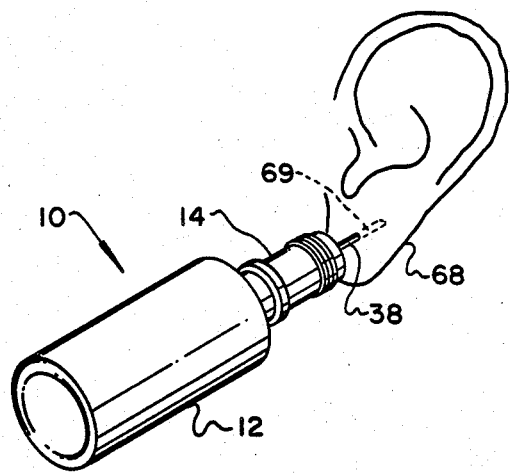
FIG. 6 is a perspective view illustrating the apparatus in a typical position in use.

Referring to FIG. 6, the aparatus 10 is illustrated in use wherein the cap 54 has been removed from the container 12 and the probe 38 has been inserted in a posthole or similar passage 69 formed in an earlobe 68 to remove foreign matter and to otherwise clear the passage. As previously mentioned, the postholes in human earlobes for the receipt of earring posts tend to become clogged and irritated. The earring postholes tend to close if not used frequently since the formation of a posthole is unnatural and the tissue defining the posthole boundaries, if not fully healed, tends to become infected and grow back in such a way as to close the posthole. Accordingly, it is desirable to frequently clear and enlarge a posthole by insertion of the probe 38 into the posthole while preferably rotating the container 12 to rotate the probe 38 about its longitudinal axis to provide somewhat of a reaming action as the tip of the probe is inserted into the posthole. This may be conveniently accomplished by the person whose earlobes are being treated, without assistance, by inserting the distal end 44 of the probe 38 into the posthole 69, for example, and slowly rotating the container 12 in one direction or the other whereby the parallel edges 46 perform a scraping action on the tissue defining the posthole. Thanks to the generously curved distal end surface 47 of the probe 38, it may be easily inserted into a clogged or partially restricted posthole, and the cooperating parallel edges 46, upon rotation of the probe 38 by rotating the container 12, perform a scraping or cleaning action. During the probe insertion and twisting or rotating process the container 12 may be squeezed to deflect the cylindrical sidewall 13 inwardly, as indicated by the dashed line in FIG. 1, to force a quantity of cleaning and treating solution through the channel formed by the groove 43 into the posthole to assist in the cleaning action and to serve as a germicide to alleviate any inflamation or infection of the earlobe tissue defining the posthole. The relatively small size of the groove 43 will allow substantially all of the solution to flow along the groove regardless of its position, due to capillary action, but in any case only a relatively small quantity fo solution need be dispensed during the cleaning process. The plug member 28 is preferably forced lightly against the earlobe 68 to form a seal to prevent leakage of solution before it enters the posthole 69.

If, after substantial use, the quantity of treating solution in the container 12 is exhausted, the assembly of the probe 38 and the plug 28 may be removed from the container by forcibly grasping the probe along the shank portion extending from the plug 28 and deflecting it to pop the plug 28 off of the container neck 14 so that the container may be refilled. The use of the protective cap 54 also provides for the chamber 62 to become filled with treating solution just prior to the time the apparatus 10 is placed in use by turning the container 12 upside down and allowing treating solution to flow into the chamber 62 to bathe the exterior surface of the probe 38 to disinfect same prior to use of the apparatus 10. Immediately prior to use of the apparatus 10, and before removal of the cap 54 from the container neck 14, the container 12 is held upright for a brief period of time so that any solution in the chamber 62 may drain into the recess 42 and through the groove 43 into the interior chamber 22. Accordingly, upon removal of the cap 54 from the container 12 no solution will be spilled if the prior described procedure is carried out.

Figure 4:
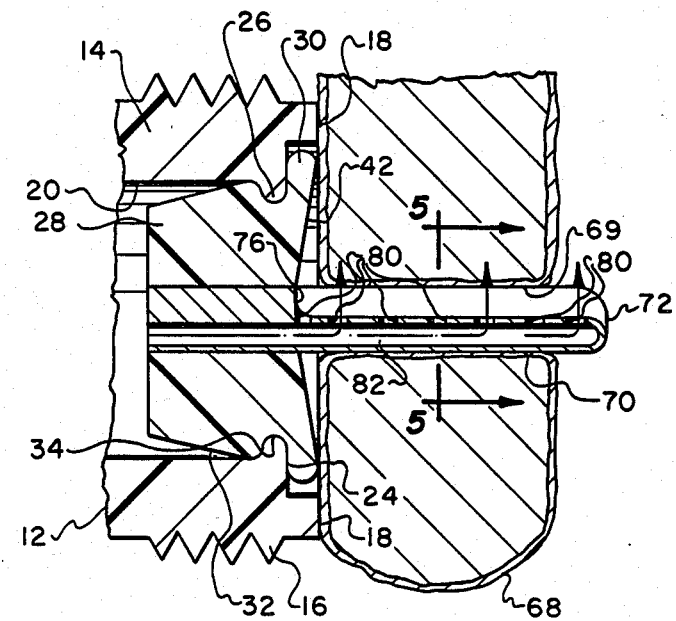
FIG. 4 is a partial longitudinal central section view of an alternate embodiment of the probe.
Figure 5:
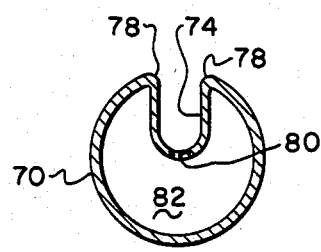
FIG. 5 is a section view taken along the line 5—5 of FIG. 4.

Referring now to FIGS. 4 and 5, an alternate embodiment of the probe for use with the plug 28 and the container 12 is illustrated and generally designated by the numeral 70. The probe 70 also comprises an enlongated cylindrical pin having a substantially hemispherical distal end 72 and a longitudinally extending groove 74 which extends from the end 72 to a transverse wall 76. The wall 76 is preferably coplanar with the surface of the recess 42 on the plug 28. The intersection of the flanks of the groove 74 with the outer circumferential surface of the probe 70 is defined by two parallel slightly curved edges 78 which are operable to scrape the tissue forming the posthole passage in the same manner as the way in which the probe 38 is utilized. The base of the groove 74 is provided with a series of spaced apart orifices 80 which open into an internal channel 82 extending from the distal end 72 through the length of the probe 70 and opening into the interior of the container 12. Accordingly, fluid used for cleaning and treating the tissue defining an earring posthole may be dispensed from the container 12 through the passage 82 and the orifices 80 into the groove 74 without as great a likelihood of spillage of fluid during use of the probe. The configuration of the probe 70 is such that, due to its small diameter, may require metal investment casting techniques on order to form the internal channel 82 and the groove 74, followed by a machining operation to drill the orifices 80. Those skilled in the art will recognize that other configurations of the probe may be provided although the provision of at least one longitudinally extending scraping edge, such as provided by the edges 46 or 78, together with means for flowing a treating solution into the posthole provides a superior cleaning and treating apparatus, particularly in conjunction with the container 12. An advantage of the probe 70 resides in the fact that, upon initial penetration of the probe into a partially blocked earring posthole, the channel 82 and the orifices 80 will permit injection of solution into the posthole even if the groove 74 becomes partially clogged or blocked with matter.

Figure 7:
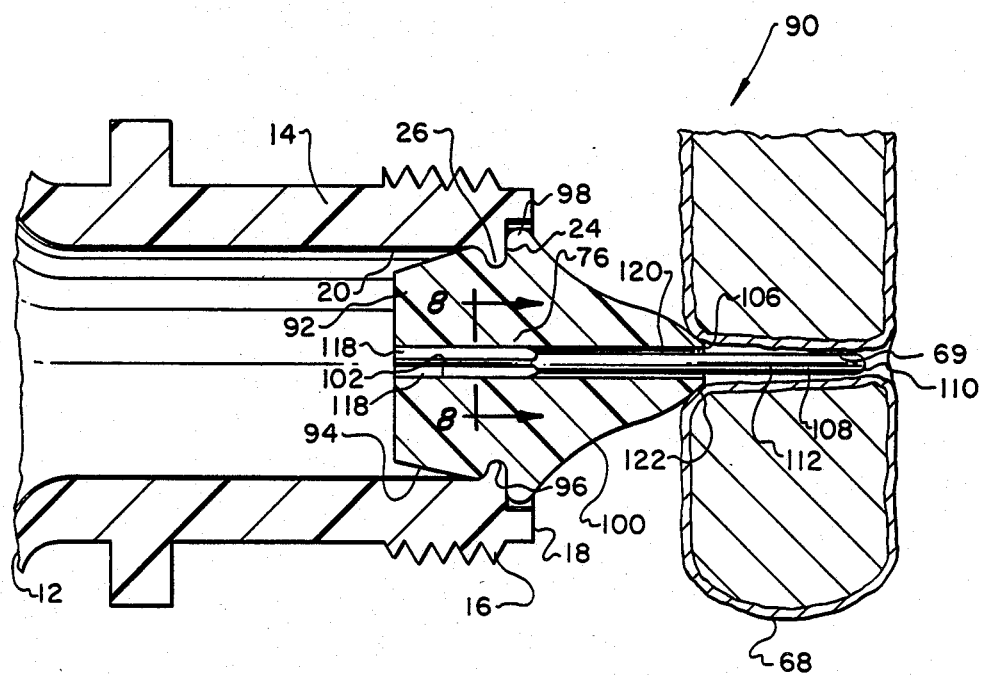
FIG. 7 is a longitudinal central section view of an alternate embodiment of an earlobe treating apparatus in accordance with the present invention.
Figure 8:
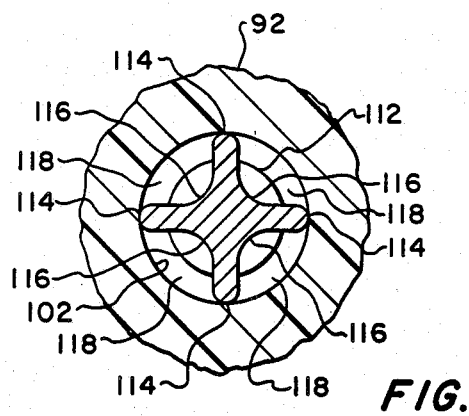
FIG. 8 is a detail section view taken along the line 8—8 of FIG. 7.

Referring now to FIGS. 7 and 8, an alternate embodiment of the apparatus of the present invention is illustrated and generally designated by the numeral 90. The apparatus 90 utilizes the container 12 but is provided with a modified plug member 92 which is forcibly insertable into the mouth 20 and includes a frusto-conical hub portion 94 and a circumferential groove 96 which receives the rim 26 in fluid-tight sealing engagement therewith. The plug 92 also includes a generally cylindrical flange 98 engageable with the transverse end face 24 when the plug member has been snapped into the position shown in FIG. 7 in the mouth of the container 12. The plug member 92 also includes a somewhat conical shaped projecting portion 100 which extends in a direction opposite to the hub 92. An elongated cylindrical bore 102 extends centrally through the plug member 92 form the hub 94 to the apex 106 of the projection 100.

The apparatus 90 also includes a modified elongated cylindrical probe member 108 having a spherical distal end 110 and an elongated cylindrical shank portion 112. The shank portion 112 blends into a portion of the probe 108 which is provided with four circumferentially spaced and radially projecting longitudinal bosses 114 which, as shown in FIG. 8, form a somewhat right angle cross configuration. Spaced apart recesses 116 are formed between each of the bosses 114. The bosses 114 are dimensioned to form a slight interference fit within the bore 102 for supporting the probe 108 in the plug member 92 with preferably a major portion of the shank 112 extending from the apex 106 of the plug member. A plurality of channels 118 are formed in the plug member 92 between the bosses 114 and the bore 102 for conducting treating solution through the bore 102 in the plug member and through an annular passage 120 formed between the bore 102 and the probe shank 112.

In use of the apparatus 90 a protective cap such as the cap 60, FIG. 1, is removed from the container neck 14 and the probe 108 is inserted into a posthole 69 of an earlobe 68 as shown by example in FIG. 7. The technique in cleaning the posthole involves gently rotating the probe 108 as the distal end 110 is forced into the posthole until the projection 100 engages the earlobe tissue adjacent to the entrance of the posthole to form a generally circumferential seal 122 between the plug projection 100 and the posthole to prevent the leakage of treatment solution from the passage 120 without being forced through the posthole. Accordingly, once the projection 100 of the plug member 92 has been lightly forcibly engaged with the earlobe 68, the container 12 may be squeezed to forcibly dispense treating solution through the passages 118 and 120 into the posthole 69 to assure that thorough flusing and cleansing action is obtained. Entry of the probe 108 into the posthole 69 may be facilitated by forcing a quantity of treating solution to flow through the passage 120 and coat the exterior surfaces of the probe to lubricate the probe as it is inserted in the posthole.

The plug member 92 and the probe 108 may be formed of the same materials as the corresponding parts of the embodiments of the invention described in conjunction with FIGS. 1 through 6. The probe member 108 may, for example, be formed of type 303 or 304 stainless steel having a diamter of the shank 112 of approximately 0.025 inches. The plug member 92 may be suitably formed of plastic as indicated in the drawing figures or of stainless steel also.

Although preferred embodiments of a cleaning and treating apparatus for earlobes having earring postholes formed therein have been described, those skilled in the art will recognize that various substitutions and modifications may be made to the specific embodiments without departing from the scope and spirit of the present invention as defined in the appended claims.

What we claim is:

1. Apparatus for treating an earlobe which has been pierced to form an ear ornament posthole, said apparatus comprising:
   a container having a flexible sidewall responsive to a squeezing action to dispense a liquid cleaning solution from an interior chamber formed by said container;
   a plug member closing one end of said container, said plug member having a projection forming a generally conical exterior surface and delimited by an apex and a bore extending through said plug member from said apex and opening into said chamber;
   an solid elongated probe member having a generally solid cylindrical shank portion and being supported at one end in said bore in said plug member by means forming a plurality of radially projecting bosses extending in said bore, said probe member having a distal end insertable in said posthole, said probe member including liquid conducting passage means formed between said bosses and said plug member and between said shank portion and said probe member within said bore for dispensing said solution into said posthole when said probe member is inserted therein, said projection being engageable with said earlobe around said posthole to form a seal to prevent leakage of said solution entering said posthole around said probe member.

2. Apparatus for treating earlobes which have been pierced to form ear ornament postholes, said apparatus comprising:
   a flexible container including an interior chamber for containing a quantity of liquid cleaning and treating solution;
   a plug member closing one end of said container, and having a bore extending to said chamber and adapted to support a probe member, said plug member including a projection defining a portion of said bore and having a generally convex exterior surface terminating at an apex of said projection, said exterior surface being engageable with an earlobe upon insertion of said probe member into said post hole to form a seal around said apex to prevent leakage of fluid being transmitted from said container;
   a slender elongated probe member supported by said plug member and having a distal end insertable in said post hole, said probe member forming liquid conducting passage means extending from flow receiving communication with said chamber toward said distal end of said probe member for conducting said solution to clean tissue defining said post hole upon insertion of said probe member in said posthole, said passage means comprising an elongated groove opening to a lateral side of said probe member and including an elongated channel formed in said probe member and opening laterally at spaced apart points into said elongated groove in said probe member, toward the exterior of said probe member for dispensing said solution into said post hole when said probe is inserted therein, and means for scraping the tissue defining said post hole by rotation of said probe member comprising opposed parallel edges of the groove at the outer circumference of said probe member.

3. Apparatus for treating earlobes which have been pierced to form ear ornament postholes, said apparatus comprising:
   a flexible container including an interior chamber for containing a quantity of liquid cleaning and treating solution;
   a plug member closing one end of said container, said plug member being removably secured in an opening in a neck of said container by cooperating rim and groove means on said container and said plug member whereby said plug member may be snapped into and out of sealing engagement with said container;
   an elongated probe member supported in a bore formed in said plug member, said probe member having a distal end insertable in said posthole and including a plurality of radially projecting bosses engaged with said plug member for supporting said probe member in said bore and forming liquid conducting passage means extending from flow receiving communication with said chamber toward said distal end of said probe member for conducting said solution to clean tissue difining said posthole upon insertion of said probe member in said posthole.

4. Apparatus for treating earlobes which have been pierced to form ear ornament postholes, said apparatus comprising:
   a flexible container including an interior chamber for containing a quantity of liquid cleaning and treating solution;
   a plug member closing one end of said container, said plug member being removably secured in an opening in a neck of said container by cooperating rim and groove means on said on said container and said plug member whereby said plug member may be snapped into and out of sealing engagement with said container;
   an elongated probe member supported in a bore formed in said plug member, said probe member having a distal end insertable in said posthole and including a plurality of radially projecting bosses engaged with said plug member, for supporting said probe member in said bore and forming liquid conducting passage means, said passage means extending from flow receiving communication with said chamber toward said distal end of said probe member, for conducting said solution to clean tissue difining said posthole upon insertion of said probe member in said posthole;
   said plug member includes a projection defining a portion of said bore and having a generally convex exterior surface terminating at an apex of said projection, said exterior surface being engageable with an earlobe upon insertion of said probe member into said posthole to form a seal around said apex to prevent leakage of fluid out of said passage means before entering said posthole.

* * * * *